(12) United States Patent
Geller

(10) Patent No.: US 9,943,679 B2
(45) Date of Patent: Apr. 17, 2018

(54) STOPCOCK ON A CATHETER-LIKE OR A SHEATH-LIKE MEDICAL INSTALLATION

(71) Applicant: Johan-Christoph Geller, Weimar (DE)

(72) Inventor: Johan-Christoph Geller, Weimar (DE)

( * ) Notice: Subject to any disclaimer, the term of this patent is extended or adjusted under 35 U.S.C. 154(b) by 0 days.

(21) Appl. No.: 15/146,174

(22) Filed: May 4, 2016

(65) Prior Publication Data

US 2016/0243349 A1 Aug. 25, 2016

Related U.S. Application Data

(63) Continuation-in-part of application No. 13/016,268, filed on Jan. 28, 2011, now abandoned.

(51) Int. Cl.
*A61M 39/22* (2006.01)
*A61B 5/15* (2006.01)

(52) U.S. Cl.
CPC ..... *A61M 39/223* (2013.01); *A61B 5/150221* (2013.01); *A61B 5/150992* (2013.01); *A61M 2039/229* (2013.01)

(58) Field of Classification Search
CPC ................ A61M 39/22; A61M 39/223; A61M 2039/229
See application file for complete search history.

(56) References Cited

U.S. PATENT DOCUMENTS

| | | | | |
|---|---|---|---|---|
| 3,057,350 A | * | 10/1962 | Cowley | A61M 39/223 137/607 |
| 3,716,259 A | * | 2/1973 | Weill | B65D 9/34 220/683 |
| 3,983,997 A | * | 10/1976 | Warshaw | B65D 75/004 206/389 |
| 4,608,996 A | * | 9/1986 | Brown | A61B 5/0215 600/348 |
| 4,621,022 A | * | 11/1986 | Kohaut | B65D 81/09 206/523 |
| 4,955,471 A | * | 9/1990 | Hirose | B65D 85/672 206/303 |
| 5,046,528 A | * | 9/1991 | Manska | F16K 31/602 137/385 |
| 5,098,393 A | * | 3/1992 | Amplatz | A61M 25/0606 604/167.03 |
| 5,135,026 A | * | 8/1992 | Manska | A61M 39/22 137/555 |
| 5,199,229 A | * | 4/1993 | Herold | A61C 3/025 433/116 |
| 5,315,762 A | * | 5/1994 | Dearman | A01G 3/065 30/231 |
| 5,988,220 A | | 11/1999 | Sakaki | |
| 2007/0233046 A1 | | 10/2007 | Funamura et al. | |

FOREIGN PATENT DOCUMENTS

| | | |
|---|---|---|
| DE | 102007049126 A1 | 4/2009 |
| EP | 2168628 A1 | 3/2010 |
| WO | 2006025054 A2 | 3/2006 |

* cited by examiner

*Primary Examiner* — Kami A Bosworth

(57) ABSTRACT

A stopcock having a deflectable stopcock lever. Said stopcock is fixedly connected to a catheter-like or sheath-like medical installation for supplying drugs into a blood vessel of a patient or an animal or for withdrawing blood from the vessel, with a blocking device being provided on the stopcock, ensuring trouble-free retraction of the medical installation from the vessel or replacement of the medical installation. This is preferably a three-way stopcock.

9 Claims, 3 Drawing Sheets

STOPCOCK ON A CATHETER-LIKE OR A SHEATH-LIKE MEDICAL INSTALLATION

FIELD OF THE INVENTION

The present invention relates to a stopcock having a deflectable stopcock lever. The stopcock is fixedly connected as the end part to a catheter-like or charging sheath-like medical installation for supplying medicines into a vessel of a patient or for withdrawing body fluid from a vessel. In other words, the stopcock is attached to a free end of an intravascular catheter-like or sheath-like medical installation like an intravascular introducer sheath for supplying pharmaceutical drugs to a human or animal blood vessel or for controlled withdrawal of body fluids from a human or animal vessel, for example, in tests on the heart. A stopcock according to the present invention may also be attached to an introducer sheath for catheter insertion into the vasculature and the heart.

BACKGROUND OF THE INVENTION

The use of three-way valves at the proximal end of catheters or intravascular charging sheaths is well known in medical technology. In this field, such a three-way valve is also called a 3-way-stopcock. The stopcock comprises a stopcock housing having connections leading away from the stopcock housing. A stopcock body having a control channel is mounted in the stopcock housing. Said stopcock body is connected with a stopcock lever in a fixed manner for rotating the stopcock body within the stopcock housing. When an intravascular introducer sheath is positioned in a patient's blood vessel, a drug may be dispensed through the introducer sheath into the vessel at any one of the three connections of a three-way stopcock, depending on the position of the stopcock lever.

In the case of a cardiac catheter examination and especially in the course of electro-physiologic studies where multiple catheters have to be introduced, for example, more than one catheter and charging sheath are frequently needed in the immediate vicinity in addition to the introducer sheath.

In the valve cutoff position of the three-way stopcock to the introducer sheath, the stopcock lever usually points in the direction of the introducer sheath. In the current way of construction, the control lever of the three-way stopcock in this closed position may easily become snagged or jammed with the additional catheters and charging sheaths being used during a cardiac catheter examination, for example. When the introducer sheath is retracted out of the vessel or replaced using a guide wire, this can lead to a number of complications that could endanger the patient or impair the treatment. The three-way stopcock in its stopcock cutoff position can act like a hook due to a gap between the stopcock lever and the tubing that connects the introducer to the 3-way stopcock, accidentally grabbing e.g. flexible parts of the introducer or cables, catheters or the like during the process of exchange. This may lead to multiple problems during the procedure.

Similar situations may be found with other configurations of stopcocks as well, e.g. in case of using a 2-way-stopcock or a 4-way-stopcock, as long as in the cutoff position of the stopcock, the stopcock lever points in the direction of the introducer charging stopcock connected via a flexible tube or the like as shown referring to FIG. 1b later in more detail.

All these applications showing the same kind of problem described before are in the field of application of the present invention.

The object of the invention is, therefore, to offer a solution to the problem which will ensure a trouble-free retraction or replacement of an introducer sheath, for example, or a catheter in the cutoff position of the three-way stopcock in which the stopcock lever points in the direction of the introducer sheath in the usual manner. The attending physician can sense this position even in weak lighting to ensure, for example, that before retraction or replacement of the introducer sheath, the three-way stopcock is in its closing position with respect to the introducer sheath, thus avoiding unwanted blood loss or air entering the lumen as bubbles and, thus, the blood vessel during retraction of the introducer sheath. When the stopcock lever is pivoted into this closing position, the stopcock lever can easily become snagged or jammed with the other catheters or charging sheaths that are additionally present in the immediate vicinity, so that it is difficult or impossible to retract the introducer sheath out of the vessel or to replace the introducer sheath by removing it from the vessel. In addition, the other introducers or catheters may also be removed by accident after being grabbed by the stopcock in its closed position. This can lead to serious problems, e.g. blood loss, difficulty in accessing the vessel again and thus, completing the procedure, or damage to the vessel.

SUMMARY OF THE INVENTION

The problem on which the invention is based is solved according to the invention in that a blocking device is provided at a free ending of the stopcock lever, where said blocking device shuts a gap being formed by parts of the stopcock lever, the stopcock housing and one of the radial connections at least in a closing state of the stopcock.

According to a preferred embodiment of the invention, the stopcock is a three-way valve or 3-way-stopcock. This type of stopcock is well known within the medical sector, where many incidents of the kind as outlined above have been reported.

In an embodiment, of the invention, it is preferred that the blocking device is arranged on the radially lengthened pipe connection of the three-way stopcock forming a tube connection to a medical installation e.g. an intravascular sheath. Further, the blocking device may be arranged on the control lever of the three-way stopcock.

In a preferred embodiment of the invention, the three-way stopcock is connected to an introducer sheath by means of a flexible tube or hose. The stopcock and the introducer sheath are mechanically decoupled. Thus, any kind of handling of the stopcock or action carried out at the stopcock does not induce any force to the introducer sheath and the opening in the body, thus preventing any damage to the vessel.

Further, in an embodiment of the invention, the blocking device claims the access from the outside into the free gap between the control lever and the tube connection to the medical installation at least in the closed state. Then, the blocking device preferably blocks access from the outside to the free gap between the control lever and the lengthened pipe connection of the stopcock. It may be further advantageous that the blocking device is arranged on the front end of the stopcock lever. According to an alternative embodiment, the blocking device is arranged on the lengthened pipe connection. Last but not least, the stopcock lever or the pipe connection may be designed in one piece with the blocking device.

The invention is not limited to the features in the claims. On the basis of these features, alternative approaches that are readily self-evident to the skilled person in the art, all of which are within the scope of the general inventive idea, are suggested here.

BRIEF DESCRIPTION OF THE DRAWINGS

The invention will now be described and explained without restriction on the basis of the following drawings of embodiments of the invention, in which.

DETAILED DESCRIPTION OF THE INVENTION

Without any limitation of the present invention, the situation given with a three-way valve or stopcock is described hereafter only. However, it is obvious for the person skilled in the art to transfer the idea of the present invention to similar applications in other technical fields.

Figure 1A:
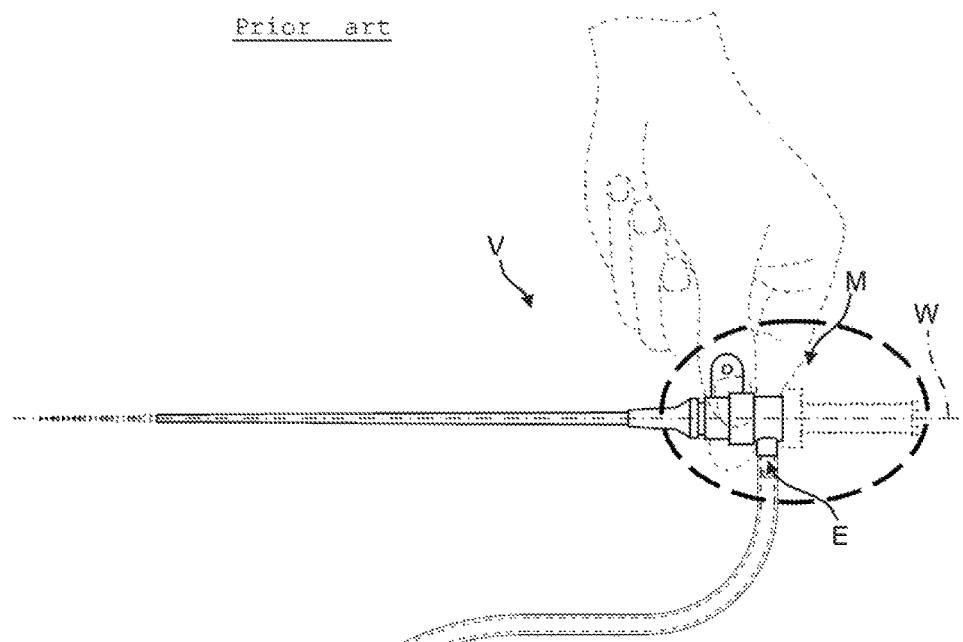
FIG. 1a shows s conventional three-way valve or stopcock, for example, in combination with an introducer charging sheath in a view from above.
Figure 1A:
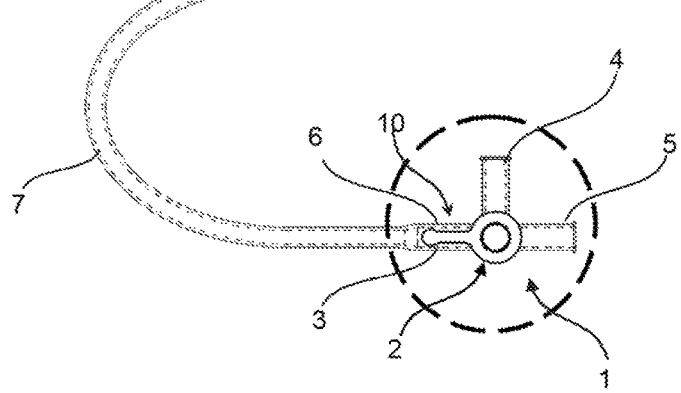
Figure 1B:
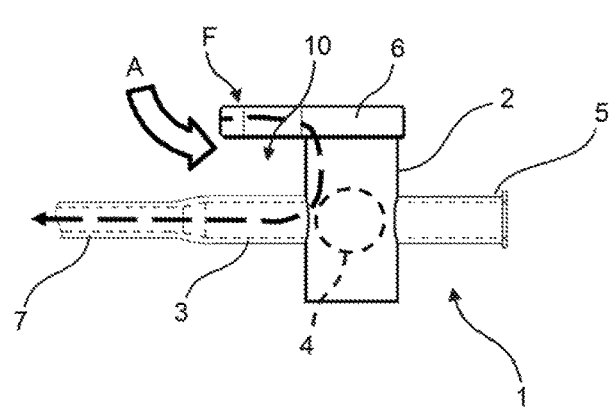
FIG. 1b shows the conventional three-way stopcock according to FIG. 1a in a side view.

FIGS. 1a and 1b show a three-way valve or three-way stopcock according to the state of the art, labeled as 1, in a view from above (FIG. 1a) and in a side view (FIG. 1b). The cylindrical stopcock, housing is labeled as 2, with three radial connections 3, 4 and 5 leading away from the stopcock housing 2, each connection forming a 90° angle to the others. A known cylindrical stopcock body having a T-shaped control channel is rotatably mounted in the cylindrical stopcock housing 2 (not shown in detail here), where the stopcock body protrudes slightly beyond the upper end of the stopcock housing 2 axially, to which a stopcock lever 6 of a predetermined length extending radially outward is connected in a rotationally fixed manner for rotating the stopcock body 2.

FIG. 1a shows the three-way stopcock 1 being connected to an introducer sheath V by means of a flexible tube or hose 7. In more detail, FIG. 1a shows the pivotable stopcock lever 6 radially in the direction of the introducer sheath V which is used here, for example, and is fixedly connected via the flexible hose 7 from a stopcock connection end E of an outer portion of the introducer sheath V to the one lengthened radial connection 3 forming a tube connection of the three-way stopcock 1. In this situation, the three-way stopcock 1 is in its closed state. Thus, as indicated in FIG. 1a, manual operations may be carried out in a region M of handling and manual operation e.g. during electro-physiologic studies.

A supply line for drugs (not shown) may be detachably connected to each of the two other connections 4 and 5 of the three-way stopcock 1. However, in a situation as shown in FIG. 1a the three-way stopcock 1 is shut and no fluid is passing to the introducer and thus to or from the blood vessel/patient/animal at all.

By rotating the stopcock lever 6 clockwise by 90° out of its closed position shown in FIGS. 1a and 1b in the direction of the connection 4 with respect to the introducer sheath V, the connection 4 is cut off, and at the same time via connection 5, fluids/drugs can be given through the open connection 3 to the introducer sheath V via the hose 7.

By further rotating the stopcock lever 6 clockwise by 90°, the stopcock lever 6 points in the direction of connection 5, in which the stopcock is cut off in this direction, and instead the connection 4 is connected to the open connection 3 to the introducer sheath V.

By further rotating the stopcock lever 6 by 90° in a direction opposite to the connection 4, both connections 4 and 5 may foe connected to the open connection 3, respectively. Medication may be dispensed into the introducer sheath through connection 3 and/or 4, depending on which position of the stopcock lever 6 is selected. However, usually the stopcock lever 6 points in the direction of connection, which is cut off.

If the stopcock lever 6 points into the gasket of one of the connections 3, 4 or 5, then, as stated previously, this shows the attending physician the closed position of the respective connection 3, 4 or 5. Thus, in the stopcock cutoff position of the three-way stopcock to the introducer sheath V, the stopcock lever 6 points in the direction of the introducer sheath V. However, this way a gap 10 is formed by parts of the stopcock lever 6, the stopcock housing 2 and the radial connection 3. Retraction of the introducer sheath V from the treated vessel or replacing the introducer sheath V is executed via a manipulation of the introducer sheath V only. The stopcock 1 connected to the introducer sheath V via the flexible tube 7 is left unattended. It has been found, that at least during said kinds of manipulation of the introducer sheath V, the stopcock 1 is able to catch other flexible tubes, electric cables of sensors, catheters that are introduced into a vessel or the like within said gap 10. This is indicated by an arrow A in FIG. 1b. In a way, the gap 10 acts like a hook. This special behavior of said group of components of the stopcock 1 forming the gap 10 in said security status is illustrated in FIG. 1b by means of the dashed line, where the arrow in dashed lines shows the normal movement of the stopcock 1 during retraction. Throughout this movement, the stopcock, lever 6 is oriented in parallel to said retraction movement, enabling said hook-like behavior. However, it has to be noted that during said process of changing an introducer sheath V usually using the left hand, the attending physician does not have a free right hand because an object, e.g. a guide wire W, has to be held and/or operated at the same time, too. Such a guide wire W is used to position e.g. a new introducer sheath V having a larger diameter. Thus, during normal operation as outlined above, there is no chance to observe vend guide the stopcock 1 to avoid its grabbing or catching other flexible tubes, catheters or the like within said gap 10.

As a consequence, each retraction of the introducer sheath V from the treated vessel may cause an unattended und undesirable retraction of at least a second introducer sheath V or the like. This may lead to a number of different kinds of fatal malfunctions within a common, everyday procedure in this field of the art e.g. in the course of electro-physiologic studies or the like. The object of the invention is, therefore, to offer a solution to the problem which will ensure a trouble-free retraction or replacement of an introducer sheath V or a catheter in the cutoff position to the three-way stopcock 1, in which the stopcock lever 6 points in the direction of the introducer sheath V in the usual manner.

In FIGS. 2 through 6, which show five exemplary embodiments, of the three-way stopcock according to the present invention without restriction, corresponding parts of the stopcock 1 are labeled with the same reference numerals as those used in FIGS. 1a and 1b. The blocking devices on the inventive three-way stopcock for trouble-free retraction of the introducer sheath. V from the treated vessel or for replacing the introducer sheath V are each labeled with reference numeral 8 as the basic numeral, differentiating them by indices a, b, c, d and e, respectively. Each of these blocking devices 8a-8e makes sure that the gap 10 at least is closed. Thus, flexible tubes, electric cables of sensors, catheters that are introduced into a vessel or the like can no longer enter into said gap 10 as indicated by the arrow & shown in dashed lines in FIG. 2.

Figure 2:
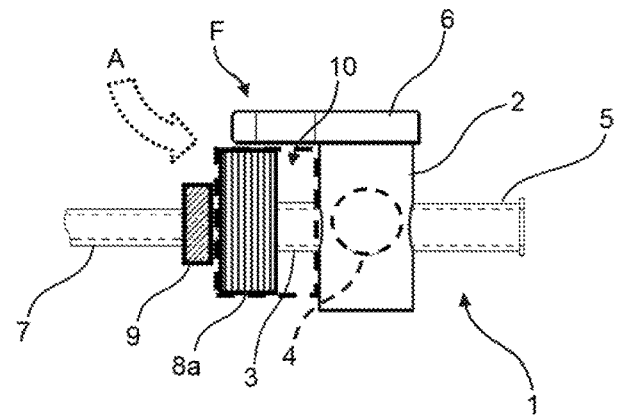
FIG. 2 shows a three-way stopcock according to the invention in a first embodiment in a side view.

The blocking device 8 in FIG. 2 consists of a ring body 8a, which is fitted to the diameter of the lengthened radial connection 3 and is pushed over the connection 3 of the three-way stopcock 1 as far as the stop on the stopcock housing 2. The ring body 8a has a radial diameter and an axial width, such that the free gap between the bottom side of the stopcock lever 6 and the top side of the connection 3 of the three-way stopcock 1 is closed in such a way that the free pivotability or rotation of the stopcock lever 6 is not hindered.

The ring-shaped blocking device 8a may be fixedly connected to the lengthened radial connection 3. However, it may also be pushed onto connection 3 as an add-on or replaceable part. In any way, said ring-shaped blocking device 8a is supplied to close the entry section of the gap 10. It is obvious to the person skilled in the art that said ring-shaped blocking device 8a may even fill the gap 10 to prevent any of the forestanding malfunctions that could occur during said manipulation of the introducer sheath V. The same applies to subsequent embodiments of the invention without further mentioning.

A securing sleeve 9, which may optionally also be omitted, is provided on the front end of the connection to prevent unintentional removal of the blocking device 8a from the connection 3.

The blocking device 8a may be made of any material which fulfills the required blocking function here, in particular foamed plastic, which has proven suitable in comparable medical installations.

Figure 3:
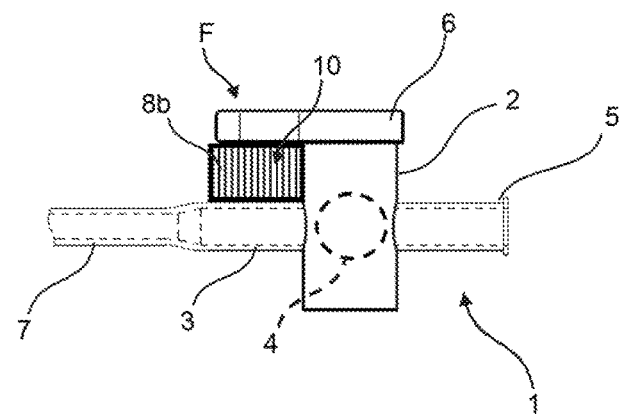
FIG. 3 shows a three-way stopcock according to the invention in a second embodiment in a side view.

In FIG. 3 the blocking device 8b comprises a strip-shaped material, which is fixedly arranged here on the bottom side of the stopcock lever 6, for example, and fills op the stopcock lever 6 for sealing the connection 3, filling the free gap 10 from the bottom side of the stopcock lever 6 up to tightly against the top side of the connection 3 in the closed position, such that the free rotation of the stopcock lever 6 is not restricted. The blocking device 8b could also be arranged on the top side of the connection 3 accordingly.

Figure 4:
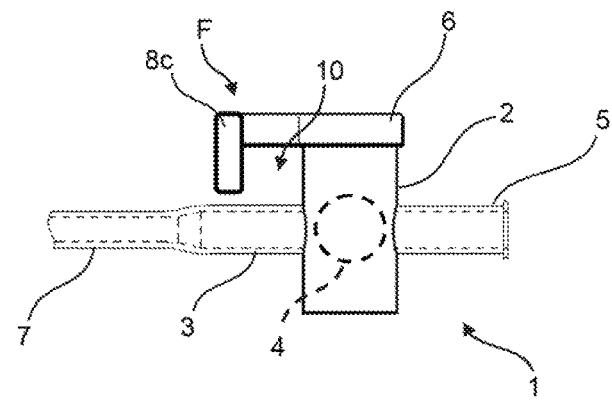
FIG. 4 shows a three-way stopcock according to the invention in a third embodiment in a side view.

In FIG. 4 the blocking device 8c is formed from a shield-like part, which is fixedly or detachably arranged on the end face of the stopcock lever 6 and protrudes only slightly beyond the upper end of the stopcock lever 6 but extends with its lower end at a right angle to the stopcock lever 6 perpendicularly downward close to the outside surface of the connection 3. In this way, the free gap 10 between the bottom side of the stopcock lever 6 and the top side of the connection 3 is closed securely from the outside to reliably prevent snagging or jamming of the stopcock lever 6 with the additional charging sheaths or catheters or the like.

Figure 5:
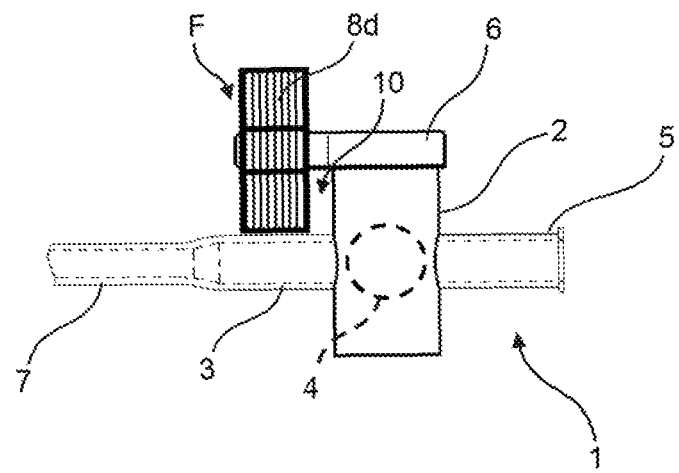
FIG. 5 shows a three-way stopcock according to the invention in a fourth embodiment in a side view.

FIG. 5 shows another variant of the blocking device 8d, which is designed as a ring-shaped body in FIG. 5, comparable to the approach in FIG. 2, and is pushed at its central opening over a radial section of the stopcock lever 6 and is arranged here fixedly or as a removable part on the stopcock lever 6. The ring body 3d here is at a small distance from the stopcock housing 2 to maintain an unhindered pivoting movement of the stopcock lever 6.

Figure 6:
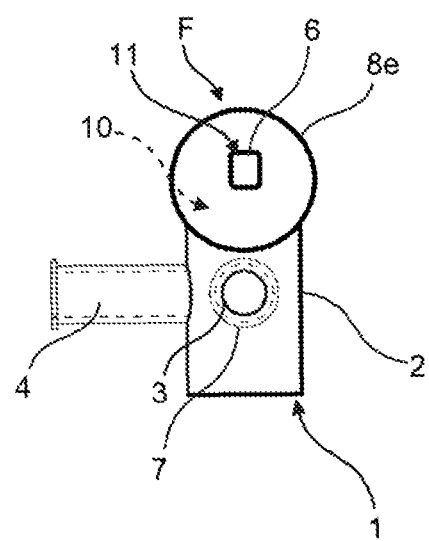
FIG. 6 shows a three-way stopcock according to the invention in a fifth embodiment in the view from the front of the connection of the stopcock to the connection to the introducer sheath (not shown in FIG. 6).

The blocking device according to FIG. 6 comprises a ring-shaped disk body 8e, which has a central opening 11 for attaching the disk-type blocking body 8e to the front end of the stopcock lever 6, so that, as in the approach according to FIG. 4, the free gap 10 between the bottom side of the stopcock lever 6 and the top side of the connection 3 is tightly closed off in a manner such that snagging or jamming with additional charging sheaths V and/or catheters is reliably prevented. Here again, the ring-shaped disk body 8e cars be fixedly connected to the outer end of the stopcock lever 6 or may also be detachably attached to the front end of the stopcock lever. The shield-like part 3c in FIG. 4 and the ring-shaped disk body 8e in FIG. 6, each one on the front end of the stopcock lever 6, may also be designed in one piece with the latter.

The variants described above for the blocking devices 8 are either fixedly or detachably arranged on the lengthened radial connection 3 for the introducer sheath V or on the stopcock lever 6. Those skilled in the art in the respective field will readily obtain suggestions for additional variants within the scope of the present inventive idea from these embodiments of the invention for trouble-free handling, for example, an introducer sheath V connected to a three-way stopcock 1.

The blocking devices according to the invention ensure that on retraction of an introducer sheath V out of a blood vessel, for example, or on replacement of the introducer sheath V, the stopcock lever 6 of the three-way stopcock 1 is not snagged or jammed with additional catheters or introducer sheaths V, so that retraction or replacement of the introducer sheath V is blocked or made difficult and is possible only after a time lag, after which the jamming or snagging with the other charging sheaths V and/or catheters has been resolved.

The invention claimed is:

1. A stopcock assembly configured to be fixedly connected as an end part to a catheter-like or charging sheath-like medical installation for supplying medicines into a vessel of a patient or for withdrawing body fluid from a vessel, the stopcock assembly comprising:
   a stopcock comprising
      a stopcock housing having a plurality of radial connections leading away from the stopcock housing; and
      a stopcock body having a control channel, the stopcock body being mounted in the stopcock housing and connected with a stopcock lever in a fixed manner for rotating the stopcock body within the stopcock housing; and
   a detachable blocking device attached to the stopcock in a detachable manner, wherein said blocking device blocks free access to a gap formed by a free end of the stopcock lever, the stopcock housing, and one of the radial connections at least in a closing state of the stopcock.

2. The stopcock assembly according to claim 1, wherein the stopcock is a three-way valve.

3. The stopcock assembly according to claim 2, wherein the blocking device is arranged on the one of the radial connections of the three-way valve, wherein the one of the radial connections is lengthened and is configured to be connected to the medical installation.

4. The stopcock assembly according to claim 2, wherein the stopcock is configured to be connected to an introducer sheath of the medical installation by a flexible tube of the medical installation or by a hose of the medical installation.

5. The stopcock assembly according to claim 2, wherein the blocking device is arranged on the stopcock lever of the three-way valve.

6. The stopcock assembly according to claim 1, wherein the blocking device blocks access from outside into the gap between the stopcock lever and the one of the radial connections, wherein the one of the radial connections is lengthened and is configured to be connected to the medical installation.

7. The stopcock assembly according to claim 1, wherein the blocking device blocks access from outside into the gap between the stopcock lever and the one of the radial connections of the stopcock.

8. The stopcock assembly according to claim 7, wherein the blocking device is arranged on the free end of the stopcock lever.

9. The stopcock assembly according to claim 7, wherein the blocking device is arranged on the one of the radial connections, wherein the one of the radial connections is lengthened and is configured to be connected to a flexible tube of the medical installation.

* * * * *